United States Patent [19]
Price et al.

[11] Patent Number: 6,103,529
[45] Date of Patent: Aug. 15, 2000

[54] ANIMAL CELL CULTURE MEDIA COMPRISING PEPTIDES DERIVED FROM RICE

[75] Inventors: Paul J. Price, Grand Island; Steve Gorfien, Williamsville; Douglas Danner, Wilson, all of N.Y.

[73] Assignee: Life Technologies, Inc., Rockville, Md.

[21] Appl. No.: 08/949,142

[22] Filed: Oct. 10, 1997

Related U.S. Application Data

[60] Provisional application No. 60/028,197, Oct. 10, 1996.

[51] Int. Cl.$^7$ .............................. C12N 5/00; C12N 5/02
[52] U.S. Cl. ......................... 435/404; 435/390; 435/325
[58] Field of Search .................................. 435/404, 390

[56] References Cited

U.S. PATENT DOCUMENTS

| | | | |
|---|---|---|---|
| 3,622,453 | 11/1971 | Akeyama et al. | 195/29 |
| 5,122,469 | 6/1992 | Mather et al. | 435/240.2 |
| 5,318,906 | 6/1994 | Sakata et al. | 435/240.2 |
| 5,324,524 | 6/1994 | Durnford et al. | 424/520 |
| 5,372,943 | 12/1994 | Inlow et al. | 435/240.31 |
| 5,474,931 | 12/1995 | DiSorbo et al. | 435/240.31 |
| 5,607,852 | 3/1997 | Provost et al. | 435/404 |
| 5,633,162 | 5/1997 | Keen et al. | 435/384 |
| 5,741,705 | 4/1998 | Blom et al. | 435/348 |

FOREIGN PATENT DOCUMENTS

| | | |
|---|---|---|
| 01075430 | 3/1989 | Japan . |
| 2-49579 | 2/1990 | Japan . |
| 7-165524 | 6/1995 | Japan . |
| 9-40693 | 2/1997 | Japan . |
| 901673 | 7/1962 | United Kingdom . |
| WO 98/24883 | 6/1998 | WIPO . |

OTHER PUBLICATIONS

Freshney eR.I. "Culture of Animal Cells. A Manual of Basic Tecnique." Alan R.Liss, Inc., New York, 1987, pp. 74–84.

Auricchio, S., et al., "Prevention by Mannan and other Sugars of in Vitro Damage of Rat Fetal Small Intestine Induced by Cereal Prolamin Peptides Toxic for Human Celiac Intestine," *Ped. Res.* 22:703–707 (1987).

Coleman, W.H., and Roberts, W.K., "Inhibitors of Animal Cell–Free Protein Synthesis from Grains," *Biochim. Biophys. Acta* 696:236–244 (1982).

Gibco BRL Life Technologies, Gaithersburg, Maryland 1993–1994 Catalogue and Reference Guide pp. 1–115, 4–49, 4–50, 4–61, 4–63 (1993).

Ham, R.G., "Formulation of Basal Nutrient Media," in *Methods for Preparation of Media, Supplements, and Substrata for Serum–Free Animal Cell Culture*, Barnes, D.W., et al., eds., Alan R. Liss, Inc., New York, NY, p. 3–21 (1984).

Keay, L., "Autoclavable Low Cost Serum–Free Cell Culture Media. The Growth of L Cells and BHK Cells on Peptones," *Biotechnol. Bioeng.* 17:745–764 (1975).

Keay, L., "The Growth of L–Cells and Vero Cells on an Autoclavable MEM–Peptone Medium," *Biotechnol. Bioeng.* 19:399–411 (1977).

Lambert, K.J., and Birch, J.R., "Cell Growth Media," in *Animal Cell Biotechnology* vol. 1, Spier, R.E., and Griffiths, J.B., eds., Academic Press, New York, NY, pp. 85–122 (1985).

Lasfargues, E.Y., et al., "A Serum Substitute That Can Support the Continuous Growth of Mammary Tumor Cells," In Vitro 8:494–500 (1973).

Maurer, H.R., "Towards Chemically–defined, Serum–free Media for Mammalian Cell Culture," in *Animal cell culture: a practical approach*, Freshney, R.I., eds., IRL Press, Washington, DC, pp. 13–31 (1986).

Quest International, Bioproducts Group, Product Information, Norwich, NY, for HY–YEST 444 (Jun. 1995).

Quest International, Bioproducts Group, Product Information, Norwich, NY, for HYPEP 8382 (May 1995).

Quest International, Bioproducts Group, Product Information, Norwich, NY, for HYPEP DEV 4301 I (May 1995).

Quest International, Bioproducts Group, Product Information, Norwich, NY, for HY–SOY® (Jan. 1995).

Quest International, Bioproducts Group, Product Information, Norwich, NY, for HYPEP DEV 5115 (May 1995).

Schlaeger, E.–J., "The protein hydrolysate, Primatone RL, is a cost–effective multiple growth promoter of mammalian cell culture in serum–containing and serum–free media and displays anti–apoptosis properties," *J. Immunol. Meth.* 194:191–199 (Aug. 1996).

Strober, W., et al., "The Pathogenesis of Gluten–Sensitive Enteropathy," *Ann. Int. Med.* 83:242–256 (1975).

Waymouth, C., "Preparation and Use of Serum–Free Culture Media," in *Methods for Preparation of Media, Supplements, and Substrata for Serum–Free Animal Cell Culture*, Barnes, D.W., et. al., eds., Alan R. Liss, Inc., New York, NY, pp. 23–68 (1984).

Wyss, C., "Cloning of Drosophila Cells: Effect of Vitamins and Yeast Extract Components," *Somatic Cell Genet.* 5:23–28 (1979).

Dialog File 351, Accession No. 90–096513, Derwent WPI English language abstract for JP 2–49579, Feb. 1990.

Dialog File 351, Accession No. 97–175705, Derwent WPI English language abstract for JP 9–40693, Feb. 1997.

Dialog File 351, Accession No. 95–261164, Derwent WPI English language abstract for JP 7–165524, Jun. 1995.

*Primary Examiner*—Sandra E. Saucier
*Assistant Examiner*—Vera Afremova
*Attorney, Agent, or Firm*—Sterne, Kessler, Goldstein & Fox P.L.L.C.

[57] ABSTRACT

The present invention provides serum-free cell culture media formulations which are capable of supporting the in vitro cultivation of animal cells. The media comprise at least one nutrient of plant derivation, such as at least one plant peptide and/or at least one plant lipid and/or at least one plant fatty acid. The media may further optionally comprise an enzymatic digest or extract of yeast cells. The present invention also provides methods of cultivating animal cells in vitro using these cell culture media formulations. In addition, the media of the present invention can be used for growth of animal cells for virus production.

In particular, an animal cell culture medium comprising at least one peptide derived from rice, wherein said animal cell culture medium is completely devoid of animal-derived proteins.

26 Claims, No Drawings

ANIMAL CELL CULTURE MEDIA COMPRISING PEPTIDES DERIVED FROM RICE

CROSS REFERENCE TO RELATED APPLICATION

This application claims priority to U.S. Provisional Patent Application No. 60/028,197, filed Oct. 10, 1996, the contents of which are entirely incorporated herein by reference.

BACKGROUND OF THE INVENTION

1. Field of the Invention

The present invention relates generally to cell culture medium formulations. Specifically, the present invention provides cell culture medium formulations which comprise one or more plant peptides for facilitating the in vitro cultivation of animal cells. The present invention also relates to media formulations which comprise one or more plant lipids and/or fatty acids for cultivation of animal cells in vitro. The formulations of the invention may also comprise one or more plant peptides and one or more plant lipids or fatty acids. In accordance with the invention, such plant-derived peptides, lipids and/or fatty acids may be used as substitutes for one or a number of animal-derived culture media components. The invention also provides methods for cultivating animal cells using these plant nutrient-based culture media. The media of the present invention are particularly suited for virus production in animal cells.

2. Related Art

Cell Culture Media

Cell culture media provide the nutrients necessary to maintain and grow cells in a controlled, artificial and in vitro environment. Characteristics and compositions of the cell culture media vary depending on the particular cellular requirements. Important parameters include osmolarity, pH, and nutrient formulations.

Media formulations have been used to cultivate a number of cell types including animal, plant and bacterial cells. Cells cultivated in culture media catabolize available nutrients and produce useful biological substances such as monoclonal antibodies, hormones, growth factors and the like. Such products have therapeutic applications and, with the advent of recombinant DNA technology, cells can be engineered to produce large quantities of these products. Cultured cells are also routinely used for the isolation, identification and growth of viruses. Thus, the ability to cultivate cells in vitro is not only important for the study of cell physiology, but is also necessary for the production of useful substances which may not otherwise be obtained by cost-effective means.

Cell culture media formulations have been well documented in the literature and a number of media are commercially available. In early cell culture work, media formulations were based upon the chemical composition and physicochemical properties (e.g., osmolality, pH, etc.) of blood and were referred to as "physiological solutions" (Ringer, S., *J. Physiol.* 3:380–393 (1880); Waymouth, C., In: *Cells and Tissues in Culture*, Vol. 1, Academic Press, London, pp. 99–142 (1965);Waymouth, C., In Vitro 6:109–127 (1970)). However, cells in different tissues of the mammalian body are exposed to different microenvironments with respect to oxygen/carbon dioxide partial pressure and concentrations of nutrients, vitamins, and trace elements; accordingly, successful in vitro culture of different cell types will often require the use of different media formulations. Typical components of cell culture media include amino acids, organic and inorganic salts, vitamins, trace metals, sugars, lipids and nucleic acids, the types and amounts of which may vary depending upon the particular requirements of a given cell or tissue type.

Typically, cell culture media formulations are supplemented with a range of additives, including undefined components such as fetal bovine serum (FBS) (10–20% v/v) or extracts from animal embryos, organs or glands (0.5–10% v/v). While FBS is the most commonly applied supplement in animal cell culture media, other serum sources are also routinely used, including newborn calf, horse and human. These types of chemically undefined supplements serve several usefull functions in cell culture media (Lambert, K. J. et al., In: *Animal Cell Biotechnology*, Vol. 1, Spier, R. E. et al., Eds., Academic Press New York, pp. 85–122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum and/or animal extracts are commonly used as relatively low-cost supplements to provide an optimal culture medium for the cultivation of animal cells.

Unfortunately, the use of serum or animal extracts in tissue culture applications has several drawbacks (Lambert, K. J. et al., In: *Animal Cell Biotechnology*, Vol 1, Spier, R. E. et al., Eds., Academic Pres New York, pp. 85–122 (1985)). For example, the chemical composition of these supplements may vary between lots, even from a single manufacturer. The supplements of animal or human origin may also be contaminated with infectious agents (e.g., mycoplasma and viruses) which can seriously undermine the health of the cultured cells when these contaminated supplements are used in cell culture media formulations and may pose a health risk in cell therapy and other clinical applications. A major fear is the presence of prions causing spongiform encephalopathy in humans or animals. Cell surface chemistry, which is a critical portion of the in vitro microenvironment for many cell types, can be adversely modified via adsorption or incorporation of serum or extract proteins. The use of undefined components such as serum or animal extracts also prevents the true definition and elucidation of the nutritional and hormonal requirements of the cultured cells, thus eliminating the ability to study, in a controlled way, the effect of specific growth factors or nutrients on cell growth and differentiation in culture. Moreover, undefined supplements prevent the researcher from studying aberrant growth and differentiation and the disease-related changes in cultured cells. Using cell culture media in the industrial production of biological substances, serum and animal extract supplementation of culture media can also complicate and increase the costs of the purification of the desired substances from the culture media due to nonspecific co-purification of serum or extract proteins.

Serum-Free Media

To overcome these drawbacks of the use of serum or animal extracts, a number of serum-free media have been developed. These media, which often are specifically formulated to support the culture of a single cell type, incorporate defined quantities of purified growth factors, lipoproteins and other proteins usually provided by the serum or extract supplement. Since the components (and concentrations thereof) in such culture media are precisely known, these media are generally referred to as "defined culture media" and often as "serum-free media" or "SFM." A number of SFM formulations are commercially available, such as those designed to support the culture of endothelial cells, keratinocytes, monocytes/macrophages, fibroblasts, neurons, lymphocytes, chondrocytes or hepatocytes which are available from Life Technologies, Inc. (Rockville, Md.).

SFM generally provide several distinct advantages to the user. For example, the use of SFM facilitates the investigation of the effects of a specific growth factor or other medium component on cellular physiology, which may be masked when the cells are cultivated in serum- or extract-containing media. In addition, SFM typically contain much lower quantities of protein (indeed, SFM are often termed "low protein media") than those containing serum or extracts, rendering purification of biological substances produced by cells cultured in SFM far simpler and more cost-effective.

Some extremely simple SFM, which consist essentially of vitamins, amino acids, organic and inorganic salts and buffers have been used for cell culture. Such media (often called "basal media"), however, are usually seriously deficient in the nutritional content required by most animal cells. Accordingly, most SFM incorporate into the basal media additional components to make the media more nutritionally complex, but to maintain the serum-free and low protein content of the media. Examples of such components include serum albumin from bovine (BSA) or human (HSA), animal-derived lipids such as human Excyte, sterols, etc., and certain growth factors or hormones derived from natural (animal) or recombinant sources.

The use of such animal-derived supplements in cell culture media, however, also has certain drawbacks. For example, there is a risk that the culture medium and/or products purified from it may be immunogenic, particularly if the supplements are derived from an animal different from the source of the cells to be cultured. Thus, if biological substances to be used as therapeutics are purified from such culture media, certain amounts of these immunogenic proteins or peptides may be co-purified and may induce an immunological reaction, up to and including anaphylaxis, in an animal receiving such therapeutics.

To overcome this potential problem, supplements derived from the same species as the cells to be cultured may be used. For example, culture of human cells may be facilitated using HSA as a supplement, while media for the culture of bovine cells would instead use BSA. This approach, however, runs the risks of introducing contaminants and adventitious pathogens into the culture medium (such as HIV or Hepatitis B virus from HSA preparations, or Bovine Spongiform Encephalopathy virus from BSA preparations), which can obviously negatively impact the use of such media in the preparation of animal and human therapeutics. In fact, for such safety reasons, the biotechnology industry and government agencies are increasingly regulating, discouraging and even forbidding the use of cell culture media containing animal-derived products which may contain such pathogens.

Non-animal Peptide Supplements

To overcome the limitations of the use of animal proteins in SFM, several attempts have been made to construct animal cell culture media that are completely free of animal proteins. For example, some culture media have incorporated extracts of yeast cells into the basal medium (see, for example, U.K. Patent Application No. GB 901673; Keay, L., *Biotechnol. Bioengin.* 17:745–764 (1975)) to provide sources of nitrogen and other essential nutrients. In another approach, hydrolysates of wheat gluten have been used, with or without addition of yeast extract, to promote in vitro growth of animal cells (Japanese Patent Application No. JP 2-49579). Still other media have been developed in which serum is replaced by enzymatic digests of meat, or of proteins such as α-lactalbumin or casein (e.g., peptone), which have been traditionally used in bacterial culture (Lasfargues, E. Y., et al., In Vitro 8(6):494–500 (1973); Keay, L., *Biotechnol. Bioeng.* 17:745–764 (1975); Keay, L., *Biotechnol. Bioeng.* 19:399–411 (1977); Schlager, E. -J., *J. Immunol. Meth.* 194:191–199 (1996)). None of these approaches, however, provided a culture medium optimal for the cultivation of a variety of animal cells. In fact, the approach using wheat peptides is likely to be quite unfavorable for culture of many animal cells and tissues, since wheat peptides are known to be toxic or to induce toxic effects in vitro and in vivo, particularly in the cells and tissues of the gastrointestinal systems of some mammals, including humans (Strober, W., et al., *Ann. Int. Med.* 83:242–256 (1975); Auricchio, S., et al., *Pediatr. Res.* 22(6):703–707 (1987)). Moreover, extracts from certain plants, including wheat, barley, rye and oats have been shown to inhibit protein synthesis in cell-free systems derived from animal cells (Coleman, W. H., and Roberts, W. K., *Biochim. Biophys. Acta* 696:239–244 (1982)), suggesting that the use of peptides derived from these plants in cell culture media may actually inhibit, rather than stimulate, the growth of animal cells in vitro.

Thus, there remains a need for a serum-free, low-protein culture medium suitable for cultivation of animal cells, which is completely devoid of animal or human proteins. Such a medium formulation will facilitate studies of the effects of growth factors and other stimuli on cellular physiology, will allow easier and more cost-effective purification of biological substances produced by cultured animal cells in the biotechnology industry, and most importantly will eliminate the risk of the introduction of adventitious animal and human pathogens. The current invention provides such an animal cell culture medium formulation.

BRIEF SUMMARY OF THE INVENTION

The present invention provides culture media formulations that support the culture of animal cells comprising plant peptides, preferably as a primary protein source. Specifically, the invention provides a cell culture medium, capable of supporting the cultivation of an animal cell in vitro, comprising at least one plant peptide which is not derived from wheat and which is most preferably derived from rice. In another aspect, the media formulations of the invention comprise at least one plant lipid and/or fatty acid. In yet another aspect, the media formulations of the invention may comprise at least one plant peptide and at least one plant lipid and/or fatty acid. The invention also provides such media formulations which further comprise an enzymatic digest or extract of yeast cells.

The invention also provides a cell culture medium, capable of supporting the cultivation of an animal cell in vitro, comprising an extract of yeast cells wherein the medium does not further comprise a wheat-derived plant peptide.

The media of the present invention may be 1× formulations, or may be concentrated as 10×–100×, most preferably as 10×, 20×, 25×, 50× or 100× formulations. The basal medium of the present invention comprises a number of ingredients, including amino acids, vitamins, organic and inorganic salts, sugars, each ingredient being present in an amount which supports the cultivation of an animal cell in vitro.

The medium of the invention may be used to culture a variety of animal cells, including insect cells (such as from Spodoptera or Trichoplusa species), avian cells and mammalian cells (including primary cells, established cell lines, CHO cells, COS cells, VERO cells, BHK cells and human cells). The present invention also provides methods of culturing animal and human cells using the culture medium formulations disclosed herein, comprising the steps of (a) contacting an animal cell with the cell culture medium of the present invention; and (b) cultivating the animal cell under conditions suitable to support its cultivation in vitro.

The present invention also relates to methods for replacing or substituting animal-derived products with plant peptides, plant lipids/fatty acids (or combinations thereof), and/or enzymatic digests or extracts of yeast cells. Such plant-derived products may be substituted for any number of animal-derived products, including but not limited to blood-derived products (e.g., serum, albumin, antibodies, fibrinogen, factor VIII, etc.), tissue or organ extracts and/or hydrolysates (e.g., bovine pituitary extract (BPE), bovine brain extract, chick embryo extract and bovine embryo extract), and animal-derived lipids and fatty acids, peptones, Excyte, sterols (e.g., cholesterol) and lipoproteins (e.g., high-density and low-density lipoproteins (HDLs and LDLs, respectively)).

The invention further provides compositions comprising the culture media of the present invention and an animal cell, including any of the animal cells described above.

Other preferred embodiments of the present invention will be apparent to one of ordinary skill in light of the following description of the invention, and of the claims.

DETAILED DESCRIPTION OF THE INVENTION

Definitions

In the description that follows, a number of terms conventionally used in the field of cell culture media are utilized extensively. In order to provide a clear and consistent understanding of the specification and claims, and the scope to be given such terms, the following definitions are provided.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "cytokine" refers to a compound that induces a physiological response in a cell, such as growth, differentiation, senescence, apoptosis, cytotoxicity or antibody secretion. Included in this definition of "cytokine" are growth factors, interleukins, colony-stimulating factors, interferons and lymphokines.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

By "cultivation" is meant the maintenance of cells in vitro under conditions favoring growth, differentiation or continued viability, in an active or quiescent state, of the cells. In this sense, "cultivation" may be used interchangeably with "cell culture" or any of its synonyms described above.

By "culture vessel" is meant a glass, plastic, or metal container that can provide an aseptic environment for culturing cells.

The phrases "cell culture medium," "culture medium" (plural "media" in each case) and "medium formulation" refer to a nutritive solution for cultivating cells and may be used interchangeably.

By "extract" is meant a composition comprising a concentrated preparation of the components of a substance, typically formed by treatment of the substance either mechanically (e.g., by pressure treatment) or chemically (e.g., by distillation, precipitation, enzymatic action or high salt treatment).

By "enzymatic digest" is meant a composition comprising a specialized type of extract, namely one prepared by treating the substance to be extracted (e.g., plant components or yeast cells) with at least one enzyme capable of breaking down the components of the substance into simpler forms (e.g., into a preparation comprising mono- or disaccharides and/or mono-, di- or tripeptides). In this context, and for the purposes of the present invention, the term "hydrolysate" may be used interchangeably with the term "enzymatic digest."

The term "contacting" refers to the placing of cells to be cultivated in vitro into a culture vessel with the medium in which the cells are to be cultivated. The term "contacting" encompasses mixing cells with medium, pipetting medium onto cells in a culture vessel, and submerging cells in culture medium.

The term "combining" refers to the mixing or admixing of ingredients in a cell culture medium formulation.

A cell culture medium is composed of a number of ingredients and these ingredients vary from one culture medium to another. A "1× formulation" is meant to refer to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See *Methods For Preparation of Media, Supplements and Substrate For Serum-Free Animal Cell Culture* Allen R. Liss, N.Y. (1984), which is incorporated by reference herein in its entirety. The osmolarity and/or pH, however, may differ in a 1× formulation compared to the culture medium, particularly when fewer ingredients are contained in the 1× formulation.

A "10× formulation" is meant to refer to a solution wherein each ingredient in that solution is about 10 times more concentrated than the same ingredient in the cell culture medium. For example, a 10× formulation of RPMI-1640 culture medium may contain, among other ingredients, 2.0 g/L L-arginine, 0.5 g/L L-asparagine, and 0.2 g/L L-aspartic acid (compare 1× formulation, above). A "10× formulation" may contain a number of additional ingredients at a concentration about 10 times that found in the 1× culture medium. As will be readily apparent, "20× formulation," "25× formulation," "50× formulation" and "100× formulation" designate solutions that contain ingredients at about 20-, 25-, 50- or 100-fold concentrations, respectively, as compared to a 1× cell culture medium. Again, the osmolarity and pH of the media formulation and concentrated solution may vary.

Formulation of Culture Media

Basal Media

The cell culture media of the present invention are aqueous-based, comprising a number of ingredients in a solution of deionized, distilled water to form "basal media." Any basal medium can be used in accordance with the present invention. Ingredients which the basal media of the present invention may include are amino acids, vitamins, organic and/or inorganic salts, trace elements, buffering salts and sugars. Preferably, the basal media of the invention comprise one or more amino acids, one or more vitamins, one or more inorganic salts, adenine sulfate, ATP, one or more trace elements, deoxyribose, ethanolamine, D-glucose, glutathione, N-[2-hydroxyethyl]piperazine-N'-[2-ethanesulfonic acid] (HEPES) or one or more other zwitterion buffers, hypoxanthine, linoleic acid, lipoic acid, insulin, phenol red, phosphoethanolamine, putrescine, sodium pyruvate, thymidine, uracil and xanthine. Each of these ingredients may be obtained commercially, for example from Sigma (Saint Louis, Mo.).

Amino acid ingredients which may be included in the media of the present invention include L-alanine, L-arginine, L-asparagine, L-aspartic acid, L-cystine, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially, for example from Sigma (Saint Louis, Mo.).

Vitamin ingredients which may be included in the media of the present invention include ascorbic acid magnesium salt, biotin, choline chloride, D-$Ca^{++}$-pantothenate, folic acid, i-inositol, menadione, niacinamide, nicotinic acid, paraaminobenzoic acid (PABA), pyridoxal, pyridoxine, riboflavin, thiamine•HCl, vitamin A acetate, vitamin $B_{12}$ and vitamin $D_2$. These vitamins may be obtained commercially, for example from Sigma (Saint Louis, Mo.).

Inorganic salt ingredients which may be used in the media of the present invention include $CaCl_2$, KCl, $MgCl_2$, $MgSO_4$, NaCl, $NaHCO_3$, $Na_2HPO_4$, $NaH_2PO_4 \cdot H_2O$ and ferric citrate chelate or ferrous sulfate chelate. These inorganic salts may be obtained commercially, for example from Sigma (Saint Louis, Mo.).

Trace elements which may be used in the media of the present invention include ions of barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc and aluminum. These ions may be provided, for example, in trace element salts such as $Ba(C_2H_3O_2)_2$, KBr, $CoCl_2 \cdot 6H_2O$, KI, $MnCl_2 \cdot 4H_2O$, $Cr(SO_4)_3 \cdot 15H_2O$, $CuSO_4 \cdot 5H_2O$, $NiSO_4 \cdot 6H_2O$, $H_2SeO_3$, $NaVO_3$, $TiCl_4$, $GeO_2$, $(NH_4)_6Mo_7O_{24} \cdot 4H_2O$, $Na_2SiO_3 \cdot 9H_2O$, $FeSO_4 \cdot 7H_2O$, NaF, $AgNO_3$, RbCl, $SnCl_2$, $ZrOCl_2ZrOCl_2 \cdot 8H_2O$, $CdSO_4 \cdot 8H_2O$, $ZnSO_4 \cdot 7H_2O$, $Fe(NO_3)_3 \cdot 9H_2O$, $AlCl_3 \cdot 6H_2O$.

The specific combinations of the above ingredients, their concentration ranges and preferred concentrations in the basal media are shown in Table 1.

Cytokines which may be used in the media of the present invention include growth factors such as epidermal growth factor (EGF), acidic fibroblast growth factor (aFGF), basic fibroblast growth factor (bFGF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF), transferrin, various interleukins (such as IL-1 through IL-18), various colony-stimulating factors (such as granulocyte/macrophage colony-stimulating factor (GM-CSF)), various interferons (such as IFN-γ) and other cytokines having effects upon hematopoietic stem cells such as stem cell factor (SCF) and erythropoietin (Epo). These cytokines may be obtained commercially, for example from Life Technologies, Inc. (Rockville, Md.) or R&D Systems (Minneapolis, Minn.), and may be either natural or recombinant. Most preferably, for culture of a wide variety of mammalian cells, the basal media will contain EGF at a concentration of about 0.1–100 nanograms/milliliter, preferably about 1–10 nanograms/milliliter, and most preferably about 5–10 nanograms per milliliter. Other cytokines, if used, may be added at concentrations that are determined empirically or as guided by the established cytokine art.

Additional ingredients that may be included in the present media are insulin (especially as insulin•$Zn^{++}$) and transferrin. These additional ingredients, available commercially (e.g., from Sigma, St. Louis, Mo.), may be formulated into the present media at the concentration ranges and preferred concentrations shown in Table 1. Ferric citrate chelate or ferrous sulfate can be used in the present media as a substitute for transferrin. Additionally, recombinant insulin may be substituted for animal- or human-derived insulin.

TABLE 1

Animal cell culture basal medium component concentrations

| Component | Component Ranges (mg/L) | A Preferred Embodiment (mg/L) | Most Preferred Embodiment (mg/L) |
|---|---|---|---|
| Amino Acids | about: | about: | about: |
| L-Alanine | 1–250 | 9 | 8.90 |
| L-Arginine.HCl | 10–500 | 400 | 390.0 |
| L-Asparagine.H$_2$O | 5–150 | 41 | 41.01 |
| L-Aspartic Acid | 5–125 | 13 | 13.30 |
| L-Cystine.2HCl | 0.1–250 | 115 | 114.67 |
| L-Cysteine.HCl.H$_2$O | 2–250 | 24 | 24.39 |
| L-Glutamic Acid | 5–250 | 11 | 10.73 |
| Glycine | 1–200 | 8 | 7.50 |
| L-Histidine.HCl.H$_2$O | 5–250 | 68 | 68.29 |
| L-Isoleucine | 5–500 | 171 | 171.34 |
| L-Leucine | 25–350 | 180 | 180.44 |
| L-Lysine.HCl | 25–500 | 226 | 225.62 |
| L-Methionine | 5–200 | 51 | 50.62 |
| L-Phenylalanine | 5–250 | 97 | 96.79 |
| L-Proline | 1–250 | 40 | 40.00 |
| L-Serine | 5–250 | 50 | 50.44 |
| L-Threonine | 10–300 | 130 | 130.43 |
| L-Tryptophan | 2–110 | 25 | 24.76 |

TABLE 1-continued

Animal cell culture basal medium component concentrations

| Component | Component Ranges (mg/L) | A Preferred Embodiment (mg/L) | Most Preferred Embodiment (mg/L) |
|---|---|---|---|
| L-Tyrosine.2Na$^+$.2H$_2$O | 5–400 | 137 | 137.16 |
| L-Valine | 5–400 | 137 | 137.38 |
| Other Components | about: | about: | about: |
| Adenine Sulfate | 0.01–75 | 10 | 10.0 |
| ATP | 0.001–0.1 | 0.1 | 0.09 |
| 2-Deoxyribose | 0.05–5.0 | 0.5 | 0.50 |
| Ethanolamine.HCl | 0.1–10 | 2 | 1.90 |
| D-Glucose | 1500–5000 | 3900 | 3902.4 |
| Glutathione | 0.005–5.0 | 1 | 0.60 |
| HEPES | 1000–5000 | 1800 | 1800.0 |
| Hypoxanthine.Na$^+$ | 0.1–15 | 2 | 1.66 |
| Linoleic Acid | 0.001–0.1 | 0.94 | 0.035 |
| Lipoic Acid | 0.01–10 | 0.08 | 0.075 |
| Insulin.Zn$^{++}$ | 0.5–50 | 5 | 5.00 |
| Phenol Red | 0.5–15 | 4 | 4.00 |
| Phosphoethanolamine | 0.1–10 | 1 | 1.20 |
| Putrescine.2HCl | 0.0001–0.01 | 0.004 | 0.004 |
| Sodium Pyruvate | 10–300 | 150 | 150.0 |
| Thymidine | 0.05–25 | 0.3 | 0.28 |
| Uracil | 0.05–10 | 0.3 | 0.30 |
| Xanthine.Na$^+$ | 0.005–1 | 0.03 | 0.03 |
| Vitamins | about: | about: | about: |
| Ascorbic Acid, Mg salt | 1–250 | 50 | 50.0 |
| Biotin | 0.01–1 | 0.08 | 0.075 |
| Choline Chloride | 1–150 | 8 | 8.00 |
| D-Ca$^{++}$-Pantothenate | 0.05–10 | 2 | 2.00 |
| Folic Acid | 0.1–10 | 2 | 2.00 |
| i-Inositol | 1–75 | 18 | 18.00 |
| Menadione | 0.001–0.1 | 0.01 | 0.01 |
| Niacinamide | 0.1–5 | 2 | 2.00 |
| Nicotinic Acid | 0.01–25 | 0.03 | 0.025 |
| PABA | 0.001–0.1 | 0.05 | 0.05 |
| Pyridoxal.HCl | 0.001–5 | 1.00 | |
| Pyridoxine.HCl | 0.005–10 | 0.03 | 0.025 |
| Riboflavin | 0.01–5 | 0.2 | 0.200 |
| Thiamine.HCl | 0.1–5 | 2 | 2.00 |
| Vitamin A Acetate | 0.01–1.0 | 0.1 | 0.14 |
| Vitamin B12 | 0.01–5 | 0.5 | 0.50 |
| Vitamin D2 | 0.01–1 | 0.1 | 0.10 |
| Trace Elements | about: | about: | about: |
| AgNO$_3$ | 0.00000001–0.0001 | 0.00009 | 0.000085 |
| AlCl$_3$.6H$_2$O | 0.00001–0.001 | 0.0006 | 0.000564 |
| Ba(C$_2$H$_3$O$_2$)$_2$ | 0.00001–0.005 | 0.001 | 0.00122 |
| CdSO$_4$.8H$_2$O | 0.00001–0.01 | 0.008 | 0.0079 |
| CoCl$_2$6H$_2$O | 0.00001–0.005 | 0.001 | 0.00113 |
| Cr(SO$_4$)$_3$.15H$_2$O | 0.0001–0.001 | 0.0003 | 0.00031 |
| CuSO$_4$.5H$_2$O | 0.00001–0.005 | 0.002 | 0.00182 |
| Fe(NO$_3$)$_3$.9H$_2$O | 0.05–5 | 0.75 | 0.7332 |
| FeSO$_4$.7H$_2$O | 0.0001–0.5 | 0.1 | 0.094 |
| GeO$_2$ | 0.000001–0.005 | 0.0003 | 0.00025 |
| H$_2$SeO$_3$ | 0.00001–0.005 | 0.002 | 0.0015 |
| KBr | 0.0000001–0.0001 | 0.00006 | 0.000056 |
| KI | 0.000001–0.0002 | 0.00009 | 0.000085 |
| MnCl$_2$.4H$_2$O | 0.0000001–0.001 | 0.0001 | 0.00014 |
| NaF | 0.00001–0.005 | 0.002 | 0.00197 |
| Na$_2$SiO$_3$.9H$_2$O | 0.001–0.2 | 0.1 | 0.094 |
| NaVO$_3$ | 0.00001–0.001 | 0.0006 | 0.00056 |
| (NH$_4$)$_6$Mo$_7$O$_{24}$.4H$_2$O | 0.00001–0.01 | 0.006 | 0.0056 |
| NiSO$_4$.6H$_2$O | 0.000001–0.0001 | 0.0001 | 0.000094 |
| RbCl | 0.000001–0.001 | 0.0007 | 0.00066 |
| SnCl$_2$ | 0.000001–0.0001 | 0.00002 | 0.000024 |
| TiCl$_4$ | 0.000001–0.001 | 0.0005 | 0.00047 |
| ZnSO$_4$.7H$_2$O | 0.0002–1.0 | 0.2 | 0.207 |
| ZrOCl$_2$.8H$_2$O | 0.00001–0.01 | 0.002 | 0.0015 |
| Inorganic Salts | about: | about: | about: |
| CaCl$_2$ | 1–500 | 120 | 120.00 |
| KCl | 1–500 | 300 | 320.00 |
| MgCl$_2$ | 1–500 | 125 | 125.00 |
| MgSO$_4$ | 10–500 | 100 | 98.0 |
| NaCl | 3000–9000 | 6000 | 5700.0 |
| NaHCO$_3$ | 100–4000 | 2200 | 2200.0 |
| Na$_2$HPO$_4$ | 1–500 | 300 | 299.75 |
| NaH$_2$PO$_4$.H$_2$O | 10–750 | 50 | 47.00 |
| Ferric Citrate Chelate | 0.01–2 | 1 | 0.60 |

Complete Media

The above ingredients, when admixed together in solution, form a "basal medium." Other basal media, however, can be equivalently used in accordance with the invention. According to the invention, at least one peptide, extract, enzymatic digest or hydrolysate of plant protein, and/or at least one plant-derived lipid and/or fatty acid, is added to a basal medium to formulate the complete culture media of the present invention.

Plants suitable as sources of proteins, peptides, lipids and/or fatty acids in formulating the culture media of the present invention include, but are not limited to, rice (*Oryza saliva*), soy (*Glycine max*), potato (*Solanum tuberosum*) and corn (*Zea mays*). Particularly preferred as a source of plant protein is rice. The use of wheat as a source of plant-derived proteins is specifically excluded from the present invention, as extracts and peptide preparations from wheat have been shown to contain inhibitors of protein synthesis in animal cell systems (Coleman, W. H., and Roberts, W. K., *Biochim. Biophys. Acta* 696:239–244 (1982)) and to induce toxic effects in certain mammalian cells, tissues and organs in vitro and in vivo (Strober, W., et al., *Ann. Int. Med.* 83:242–256 (1975); Aurrichio, S., et al., *Pediatr. Res.* 22(6):703–707 (1987)).

Plant peptides for use in formulating the culture media of the present invention may be prepared by digesting plant extracts with enzymes such as trypsin or chymotrypsin, by methods that are routine in the art. Alternatively, plant peptides in the form of enzymatic digests or hydrolysates may be obtained commercially, for example from Quest International (Norwich, N.Y.). Plant peptides are added to the basal medium at a concentration of about 10–1000 mg/liter, preferably about 50–500 mg/liter, and most preferably about 100–200 mg/liter.

In another preferred aspect, at least one plant lipid and/or fatty acid may be added to prepare the media formulations of the invention. Plant lipids/fatty acids suitable for use in the present culture media may be obtained from any of the above-described plant sources and others that will be familiar to one of ordinary skill, using methods of lipid/fatty acid isolation (for example, chromatography, particularly HPLC) that are well-known in the art. Alternatively, plant lipids/fatty acids and complexes of lipids and/or fatty acids may be obtained commercially, for example from Matreya, Inc. (Pleasant Gap, Pa.). Particularly preferred lipids/fatty acids for use in the present culture media include, but are not limited to, palmitate, stearate, oleate, linoleate, linolenate, arachidate, myristate, behenate, erucate, lignocerate, caprylate, caprate, laurate and palmitoleate. These lipids/fatty acids may be added individually or as mixtures comprising two or more of the above-described lipids/fatty acids, preferably in specific proportions as described in more detail below in Example 7. Preferably, plant lipids/fatty acids are added to a basal medium at concentrations of about 0.00001 to about 10,000 µg/ml, more preferably about 0.0001 to about 1000 µg/ml, and most preferably about 0.001 to about 100 µg/ml.

Together, the basal medium including plant-derived peptides and/or lipids/fatty acids formulate complete culture media according to the present invention. These complete media are suitable for use in the culture of a variety of animal cells, as described in more detail below. It may be preferable, however, to further enrich the nutritional content of the complete media to support faster growth and enhanced production of biologicals by the cultured cells, and to provide a more suitable environment for the culture of fastidious animal cells. To accomplish such enrichment, one or more additional nutrients derived from non-animal sources may be added to the above-described basal or complete media.

In one enriched medium of the invention, the additional nutrients added to the basal medium or complete medium may comprise extracts of yeast cells (hereinafter "yeast extract" or "YE"), and most preferably are ultrafiltered YE (hereinafter "yeast extract ultrafiltrate" or "YEU"). Such extracts may be prepared by methods generally understood by those skilled in the art of bacteriological or animal cell culture medium formulation, or may be obtained commercially, for example from Sigma (Saint Louis, Mo.), Difco (Norwood, Mass.) or Quest International (Norwich, N.Y.). YE or YEU are added to the basal or complete media described above at concentrations of about 10–8000 mg/liter, preferably about 10–100 mg/liter, and most preferably about 50–100 mg/liter. Alternatively, YE or YEU may be added to the basal media at these concentrations, in the absence of wheat-derived plant peptides, enzymatic digests of animal proteins and peptones, to formulate a suitable animal cell culture medium according to the present invention.

The medium ingredients can be dissolved in a liquid carrier or maintained in dry form. If dissolved in a liquid carrier at the preferred concentrations shown in Table 1 (i.e., a "1× formulation"), the pH of the medium should be adjusted to about 7.0–7.5, preferably about 7.1–7.4, and most preferably about 7.1–7.3. The osmolarity of the medium should also be adjusted to about 275–350 mOsm, preferably about 285–325 mOsm, and most preferably about 300–325 mOsm. The type of liquid carrier and the method used to dissolve the ingredients into solution vary and can be determined by one of ordinary skill in the art with no more than routine experimentation. Typically, the medium ingredients can be added in any order.

Preferably, the solutions comprising ingredients are more concentrated than the concentration of the same ingredients in a 1× media formulation. The ingredients can be 10-fold more concentrated (10× formulation), 20-fold more concentrated (20× formulation), 25-fold more concentrated (25× formulation), 50-fold more concentrated (50× concentration), or 100-fold more concentrated (100× formulation). More highly concentrated formulations can be made, provided that the ingredients remain soluble and stable. See U.S. Pat. No. 5,474,931, which is directed to methods of solubilizing culture media components at high concentrations.

If the media ingredients are prepared as separate concentrated solutions, an appropriate (sufficient) amount of each concentrate is combined with a diluent to produce a 1× medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.1–1.0 µm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1× sterile medium formulation. Autoclaving or other elevated temperature-based methods of sterilization are not favored, since many of the components of the present culture media are heat labile and will be irreversibly degraded by temperatures such as those achieved during most heat sterilization methods.

The optimal concentration ranges for the basal medium ingredients are listed in Table 1. These ingredients can be combined to form the basal animal cell culture medium which is then supplemented with cytokines, plant peptides and optionally (but preferably) with YE, YEU and/or one or more plant lipids/fatty acids (or combinations thereof), to formulate the complete media of the present invention. As will be readily apparent to one of ordinary skill in the art, the concentration of a given ingredient can be increased or decreased beyond the range disclosed and the effect of the increased or decreased concentration can be determined using only routine experimentation. In a preferred embodiment, the concentrations of the ingredients of the medium of the present invention are the concentrations listed in the far right column of Table 1, supplemented with cytokines, plant peptides and YE, YEU and/or one or more plant lipids/fatty acids as described above.

As will be readily apparent to one of ordinary skill in the art, each of the components of the culture medium may react with one or more other components in the solution. Thus, the present invention encompasses the formulations disclosed in Table 1, supplemented as described above, as well as any reaction mixture which forms after these ingredients are combined.

The optimization of the present media formulations was carried out using approaches described by Ham (Ham, R. G., *Methods for Preparation of Media, Supplements and Substrata for Serum-Free Animal Culture*, Alan R. Liss, Inc., New York, pp. 3–21 (1984)) and Waymouth (Waymouth, C., *Methods for Preparation of Media, Supplements and Substrata for Serum-Free Animal Culture*, Alan R. Liss, Inc., New York, pp. 23–68 (1984)). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth or continued health of the animal cells is measured.

The present invention also relates to methods for replacing or substituting animal-derived products with plant peptides, plant lipids, plant fatty acids, and/or enzymatic digests or extracts of yeast cells (or combinations thereof). Such plant- and/or yeast-derived nutrients may be substituted for any number of animal-derived culture medium components or substituents, including but not limited to blood-derived products, tissue/organ/gland extracts, animal-derived fatty acids and lipids, sterols, and lipoproteins. Preferably, blood-derived products and tissue/organ extracts are substituted in the culture media of the invention using one or more of the above-described plant-derived peptides, while animal-derived fatty acids/lipids, sterols and lipoproteins are preferably substituted with one or more of the above-described plant-derived lipids/fatty acids. Typical blood-derived products that may be replaced in accordance with this aspect of the invention include but are not limited to serum (e.g., fetal bovine serum and calf serum, human serum, etc.), plasma, albumin (e.g, bovine serum albumin or human serum albumin), antibodies, fibrinogen, factor VIII, etc. Typical tissue/organ/gland extracts that may be replaced in accordance with this aspect of the invention include but are not limited to bovine pituitary extract (BPE), bovine brain extract, chicken embryo extract and bovine embryo extract. In accordance with the invention, any animal-derived fatty acid or lipid, including saturated and unsaturated fatty acids/lipids that are well-known in the art, may be replaced with one or more of the above-described plant-derived lipids/fatty acids. Additionally, animal-derived sterols (e.g., cholesterol) and lipoproteins (e.g., high- and low-density lipoproteins (HDLs and LDLs, respectively)) may be replaced with one or more of the above-described plant-derived lipids/fatty acids in accordance with the invention. Other animal-derived medium components which may be replaced by one or more plant-derived nutrients in accordance with the invention can be easily determined by one of ordinary skill in the art by substituting one or more plant lipids/fatty acids, plant peptides and/or extracts/digests of yeast (or combinations thereof) and testing the effect of such substitution on cell growth by methods that will be familiar to the ordinarily skilled artisan (such as those methods described in the Examples below).

Use of Culture Media

Cells which can be cultivated in the medium of the present invention are those of animal origin, including but not limited to cells obtained from mammals, birds (avian), insects or fish. Mammalian cells particularly suitable for cultivation in the present media include those of human origin, which may be primary cells derived from a tissue sample, diploid cell strains, transformed cells or established cell lines (e.g., HeLa), each of which may optionally be diseased or genetically altered. Other mammalian cells, such as hybridomas, CHO cells, COS cells, VERO cells, HeLa cells, 293 cells, PER-C6 cells, K562 cells, MOLT-4 cells, M1 cells, NS-1 cells, COS-7 cells, MDBK cells, MDCK cells, MRC-5 cells, WI-38 cells, WEHI cells, SP2/0 cells, BHK cells (including BHK-21 cells) and derivatives thereof, are also suitable for cultivation in the present media. In particular, stem cells and cells used in in vitro virus production may be cultivated in the media of the present invention. Insect cells particularly suitable for cultivation in the present media include those derived from Spodoptera species (e.g., Sf9 or Sf21, derived from *Spodoptera frugiperda*) or Trichoplusa species (e.g., HIGH FIVE™ or MG1, derived from *Trichoplusa ni*). Tissues, organs, organ systems and organisms derived from animals or constructed in vitro or in vivo using methods routine in the art may similarly be cultivated in the culture media of the present invention.

Isolation of Cells

Animal cells for culturing by the present invention may be obtained commercially, for example from ATCC (Rockville, Md.), Cell Systems, Inc. (Kirkland, Wash.) or Invitrogen Corporation (San Diego, Calif.). Alternatively, cells may be isolated directly from samples of animal tissue obtained via biopsy, autopsy, donation or other surgical or medical procedure.

Tissue should be handled using standard sterile technique and a laminar flow safety cabinet. In the use and processing of all human tissue, the recommendations of the U.S. Department of Health and Human Services/Centers for Disease Control and Prevention should be followed (*Biosafety in Microbiological and Biomedical Laboratories*, Richmond, J. Y. et al., Eds., U.S. Government Printing Office, Washington, D.C. 3rd Edition (1993)). The tissue should be cut into small pieces (e.g., 0.5×0.5 cm) using sterile surgical instruments. The small pieces should be washed twice with sterile saline solution supplemented with antibiotics as above, and then may be optionally treated with an enzymatic solution (e.g., collagenase or trypsin solutions, each available commercially, for example, from Life Technologies, Inc., Rockville, Md.) to promote dissociation of cells from the tissue matrix.

The mixture of dissociated cells and matrix molecules are washed twice with a suitable physiological saline or tissue culture medium (e.g., Dulbecco's Phosphate Buffered Saline without calcium and magnesium). Between washes, the cells are centrifuged (e.g., at 200×g) and then resuspended in serum-free tissue culture medium. Aliquots are counted using an electronic cell counter (such as a Coulter Counter). Alternatively, the cells can be counted manually using a hemocytometer.

Plating of Cells

The isolated cells can be plated according to the experimental conditions determined by the investigator. The examples below demonstrate at least one functional set of culture conditions useful for cultivation of certain mammalian cells. It is to be understood, however, that the optimal plating and culture conditions for a given animal cell type can be determined by one of ordinary skill in the art using only routine experimentation. For routine culture conditions, using the present invention, cells can be plated onto the surface of culture vessels without attachment factors. Alternatively, the vessels can be precoated with natural, recombinant or synthetic attachment factors or peptide fragments (e.g., collagen or fibronectin, or natural or synthetic fragments thereof). Isolated cells can also be seeded into or onto a natural or synthetic three-dimensional support matrix such as a preformed collagen gel or a synthetic biopolymeric material, or onto feeder layers of cells. Use of attachment factors or a support matrix with the medium of the present invention will enhance cultivation of many attachment-dependent cells in the absence of serum supplementation.

The cell seeding densities for each experimental condition can be optimized for the specific culture conditions being used. For routine culture in plastic culture vessels, an initial seeding density of $0.1–1.0\times10^5$ cells per $cm^2$ or about 1.5× the plating concentration routinely used for the same cells in serum supplemented media is preferable.

Mammalian cells are typically cultivated in a cell incubator at about 37° C., while the optimal temperatures for cultivation of avian, nematode and insect cells are typically somewhat lower and are well-known to those of ordinary skill in the art. The incubator atmosphere should be humidified for cultivation of animal cells, and should contain about 3–10% carbon dioxide in air. Culture medium pH should be in the range of about 7.1–7.6, preferably about 7.1–7.4, and most preferably about 7.1–7.3.

Cells in closed or batch culture should undergo complete medium exchange (i.e., replacing spent media with fresh media) about every 2–3 days, or more or less frequently as required by the specific cell type. Cells in perfusion culture (e.g., in bioreactors or fermenters) will receive fresh media on a continuously recirculating basis.

Cell Culture Compositions

The cell culture media of the present invention may also be used to produce cell culture compositions comprising the present media and an animal cell. Animal cells preferably used in such compositions include, but are not limited to, cells obtained from mammals, birds (avian), insects or fish. Mammalian cells particularly suitable for use in such compositions include those of human origin, which may be primary cells derived from a tissue sample, diploid cell strains, transformed cells or established cell lines (e.g., HeLa), each of which may optionally be diseased or genetically altered. Other mammalian cells, such as hybridomas, CHO cells, COS cells, VERO cells, HeLa cells, 293 cells, PER-C6 cells, K562 cells, MOLT-4 cells, M1 cells, NS-1 cells, COS-7 cells, MDBK cells, MDCK cells, MRC-5 cells, WI-38 cells, SP2/0 cells, BHK cells (including BHK-21 cells) and derivatives thereof, are also suitable for use in forming the cell culture compositions of the present invention. Insect cells particularly suitable for use in forming such compositions include those derived from Spodoptera species (e.g., Sf9 or Sf21, derived from *Spodoptera frugiperda*) or Trichoplusa species (e.g., HIGH FIVE™ or MG1, derived from *Trichoplusa ni*). Tissues, organs, organ systems and organisms derived from animals or constructed in vitro or in vivo using methods routine in the art may similarly be used to form the cell culture compositions of the present invention. These cell culture compositions may be used in a variety of medical (including diagnostic and therapeutic), industrial, forensic and research applications requiring ready-to-use cultures of animal cells in serum-free media.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Materials and Methods

In each of the following examples, the following materials and methods were generally used.

VERO cultures (ATCC) were plated in 25 cm$^2$ cell culture flasks in duplicate in each medium at about 2.5×10$^5$ cells per flask in 5 ml of medium. No attachment factors or coating of the plastic surface are required for the culture of VERO cells. At 3 to 4 days the cells were removed using standard cell culture techniques. The surface of the culture was first washed with Dulbecco's Phosphate Buffered Saline (DPBS) and then 1.0 ml Trypsin-EDTA (Life Technologies, Inc.; Rockville, Md.) was added. The digest was allowed to sit on the cell surface for 3 to 5 minutes or until the cells rounded up and began to detach from the surface of the flask. The cells were completely detached by vigorous agitation against the palm of the hand and then 1.5 ml of soybean trypsin inhibitor was added to quickly neutralize enzymatic activity, The cells were counted under the microscope using trypan blue straining solution and new cultures plated at 2.5×10$^5$ cells per 25 cm$^2$ flask. Incubation was at 37° C. in 5% CO$_2$ in air. The cultures were passaged for a total of 4 subcultures and the mean cells per subculture determined from the counts of the final 3 subcultures (P2+P3+P4÷3).

Example 1

Formulation of Basal Cell Culture Medium

A 20 liter volume of distilled, deionized water (hereinafter "ddH$_2$O") was obtained and a sufficient volume (about 200–300 ml) of 5N HCl was added to decrease the pH of the water to about 0.80. To this water were added the trace elements (from 1000× stock), L-alanine (0.22 g), L-arginine•HCl (9.75 g), L-asparagine•HCl (1.02 g), L-aspartic acid (0.332 g), L-cysteine•HCl•H$_2$O (0.610 g), L-cystine•HCl (2.87 g), glycine (0.188 g), L-glutamnic acid (0.268 g), L-histidine•HCl•H$_2$O (1.707 g), L-isoleucine (4284 g), L-leucine (4.511 g), L-lysine•HCl (5.640 g), L-methionine (1.266 g), L-phenylalanine (2.420 g), L-proline (1.00 g), L-serine (1.261 g), L-threonine (3.260 g), L-tryptophan (0.619 g), L-tyrosine-disodium salt (3.429 g), L-valine (3.434 g), thymidine (0.0070 g), glutathione (0.015 g), pyridoxal•HCl (0.025 g), pyridoxine•HCl (0.00062 g), thiamine•HCl (0.05 g), MgSO$_4$ (2.45 g) and ferric citrate chelate (0.015 g). The solution was gently mixed by magnetic stirring for about 15 minutes. The pH of the solution was then adjusted to about 5.50 by adding a sufficient volume (about 20–25 ml) of 5N NaOH.

To this mixed solution were added NaH$_2$PO$_4$ (7.494 g), Na$_2$HPO$_4$ (1.175 g) and ascorbic acid Mg salt (1.25 g), and solution was again gently mixed for about 15 minutes. The pH was then adjusted to about 6.5 with 5N NaOH.

To this solution were then added ATP (0.025 g), uracil (0.0075 g), PABA (0.0012 g), D-Ca$^{++}$-pantothenate (0.05 g), riboflavin (0.005 g), NaCl (142.50 g), CaCl$_2$ (3.00 g), MgCl$_2$ (3.125 g) and EGF (0.00025 g). The solution was again gently mixed for about 15 minutes, during which time a 20 ml volume of absolute ethanol was obtained, to which were added vitamin A acetate (0.0035 g), vitamin D2 (0.0025 g), menadione (0.00025 g), lipoic acid (0.0019 g) and linoleic acid (0.00088 g). After allowing the compounds to dissolve in the ethanol, the ethanol solution was added to the 20 liter medium solution from above, and the medium solution was gently mixed for about 5 minutes.

To a 20 ml volume of ddH$_2$O were added biotin (0.0019 g), folic acid (0.05 g), hypoxanthine•Na (0.0415 g), xanthine•Na (0.0075 g) and insulin-Zn$^{++}$ (0.125 g). After allowing the compounds to dissolve in the water, this water solution was added to the 20 liter medium solution from above, and the medium solution was gently mixed for about 5 minutes.

The pH of the solution was then adjusted with 5N HCl or 5N NaOH to about 7.15±0.50. To this solution were then added adenine sulfate (0.25 g), D-glucose (97.56 g), choline chloride (0.20 g), i-inositol (0.45 g), nicotinic acid (0.00062 g), niacinamide (0.05 g), sodium pyruvate (3.75 g), 2-deoxyribose (0.0125 g), KCl (8.0 g), putrescine•2HCl (0.0015 g), phosphoethanolamine (0.03 g), vitamin B12 (0.0125 g), HEPES (45.0 g), NaHCO$_3$ (55.0 g) and phenol red (0.10 g).

This solution was gently mixed for about 10–15 minutes, the pH was then adjusted with 5N HCl or 5N NaOH to about 7.20±0.10, and ddH$_2$O was added to bring the final volume of the solution up to 25.0 liters. The osmolarity of the solution was determined to be about 310±10 mOsm. This basal medium formulation was then filtered through a low protein-binding filter cartridge and stored at 4° C. in conditions of diminished light until use.

Example 2

Plant Peptide Screen

Initial studies were designed to formulate a culture medium completely devoid of animal proteins that supports the culture of animal cells, To this end, enzymatic hydrolysates of a variety of non-animal sources were examined as supplements in the basal medium described in Example 1. Hydrolysates of wheat gluten (HYPEP 4301 I, designated below as "Wheat Hydrolysate 1", and HYPEP 8382, designated below as "Wheat Hydrolysate 2"), soy (HY-SOY) and rice (HYPEP 5115), as well as an extract of baker's yeast (HY-YEST 444) were obtained from Quest International (Norwich, N.Y.) and were formulated into the basal medium of Example 1 at 200 mg/liter. VERO cells were cultured in the various medium formulations, and cell counts determined, as described above in Materials and Methods, and were compared to those obtained in basal medium that was unsupplemented (negative control) or supplemented with 500 mg/liter human serum albumin (HSA; positive control). Results shown in Table 2 demonstrate mean cell count per 25 cm$^2$ flask over 3 subcultures and relative growth efficiency (RGE) for each of the medium formulations; RGE was calculated by dividing the mean cell count for a given medium formulation by that for the HSA control.

TABLE 2

Non-Animal Peptide Screen.

| Supplement | Mean Cell Count, × 10$^5$ | RGE |
|---|---|---|
| HSA | 44.9 | 100 |
| Yeast Extract | 31.1 | 69 |
| Wheat Hydrolysate 1 | 12.4 | 28 |
| Wheat Hydrolysate 2 | 12.4 | 28 |
| Soy Hydrolysate | 31.3 | 70 |
| Rice Hydrolysate | 35.9 | 80 |

These results demonstrate that, of the plant peptides tested as supplements for the culture media, the hydrolysate of rice performed most optimally. While yeast and soy extracts alone supported cell growth to some extent, the results obtained with rice peptide supplementation were significantly higher than those obtained with either soy or yeast extracts, and were nearly three times higher than that for wheat extracts. Thus, rice hydrolysate is favored as a supplement in animal protein-free formulations of culture media suitable for the cultivation of animal cells.

The poor performance of wheat hydrolysate as a medium supplement for the culture of animal cells is not altogether surprising, in light of the results of previous studies demonstrating that extracts of wheat gluten are toxic or induce toxic effects in certain cell types in vitro and in vivo (Strober, W., et al., *Ann. Int. Med.* 83:242–256 (1975); Auricchio, S., et al., *Pediatr. Res.* 22(6):703–707 (1987)) and can inhibit protein synthesis in cell-free systems of animal cells (Coleman, W. H., and Roberts, W. K., *Biochim. Biophys. Acta* 696:239–244 (1982)). Accordingly, the use of wheat peptides or hydrolysates is not appropriate for formulation of animal cell culture media according to the present invention.

Example 3
Titration of Rice Hydrolysate

To more closely examine their efficacy as supplements for the present media, rice hydrolysates were supplemented into basal media at differing concentrations; these media were then used to examine VERO cell growth as described above. Cell counts were compared to those obtained in basal medium that was unsupplemented (negative control) or to Earle's Modified Eagle's Medium (EMEM) supplemented with 5% fetal bovine serum (FBS; positive control). Results shown in Table 3 demonstrate mean cell count and relative growth efficiency (RGE) for each of the medium formulations; RGE was calculated as described in Example 2. In this experiment, the control contained 5% fetal bovine serum (FBS), which is commonly used to grow VERO cells but which is less efficient in the medium than is HSA.

TABLE 3

Titration of Rice Hydrolysate

| Supplement | Mean Cell Count, × 10$^5$ | RGE |
|---|---|---|
| 5% FBS | 35.9 | 100 |
| Rice, 100 mg/L | 39.5 | 110 |
| Rice, 200 mg/L | 35.9 | 100 |
| Rice, 300 mg/L | 39.2 | 109 |

Taken together, the results of this study demonstrate that the use of basal medium supplemented with rice hydrolysate at concentrations as low as 100 mg/liter support the growth of VERO cells at least as well as the use of EMEM supplemented with 5% FBS. These results thus demonstrate that rice hydrolysate at concentrations of 100–300 mg/liter is an optimal supplement for use in formulating the animal cell culture media of the present invention.

Example 4
Titration of Yeast Extract and Screening of Additional Plant Peptides

To examine additional sources of non-animal peptides and vitamins as supplements for the present media, extracts of yeast, soy and potato were obtained from Quest International and were supplemented into basal media at differing concentrations. Yeast extract (YE) was also examined as a co-supplement with rice hydrolysate. These media were then used to examine VERO cell growth as described above. Cell counts were compared to those obtained with EMEM supplemented with 5% FBS. Results shown in Table 4 demonstrate mean cell count and relative growth efficiency (RGE) for each of the medium formulations; RGE was calculated as described in Example 2.

TABLE 4

Titration of YE and Screening of Additional Plant Peptides

| Supplement | Mean Cell Count, × 10$^5$ | RGE |
|---|---|---|
| 5% FBS | 31.0 | 100 |
| Rice, 100 mg/L | 29.5 | 95 |
| Rice, 200 mg/L | 30.8 | 99 |
| Soy, 200 mg/L | 28.0 | 90 |
| Potato, 200 mg/L | 28.8 | 93 |
| YE, 100 mg/L | 32.0 | 103 |
| YE, 600 mg/L | 26.3 | 85 |
| YE, 6000 mg/L | 5.5 | 18 |
| Rice, 100 mg/L + YE, 100 mg/L | 33.2 | 107 |

These results demonstrate that supplementation of the basal medium of Example 1 with 100 mg/liter of YE, or with 200 mg/liter of either potato or soy extracts, supports the growth of animal cells approximately as well as the positive control medium supplemented with FBS. Higher concentrations of YE, however, were less optimal, and the highest concentration (6000 mg/liter) may actually have inhibited cell growth. Thus, YE, and hydrolysates of soy or potato, may be used as sources of non-animal protein for formulation of the animal cell culture media of the present invention.

Surprisingly, VERO cell growth was even more enhanced when a combination of rice hydrolysate and YE were used. In fact, the combination of 100 mg/liter of rice hydrolysate and 100 mg/liter of YE performed as well as plant peptides used at 200 mg/liter, suggesting that enhanced growth may be observed with the specific combination of rice and YE. These findings indicate that, while media comprising a single plant peptide or YE as a sole protein supplement are sufficient to support animal cell cultivation, the use of plant peptides and YE in combination in animal cell culture media may be particularly favorable.

Example 5

Use of Yeast Extract Ultrafiltrate

To more closely examine the use of yeast extract as a supplement in the present media, preparations of YE or an ultrafiltrate of YE ("YEU") were supplemented into basal media in the presence or absence of 100 mg/liter of rice hydrolysate. These media were then used to examine VERO cell growth as described above. Cell counts were compared to those obtained in EMEM supplemented with 5% FBS (positive control). Results shown in Table 5 demonstrate mean cell count and relative growth efficiency (RGE) for each of the medium formulations; RGE was calculated as described in Example 2.

TABLE 5

Titration of YE and YEU

| | Mean Cell Count, × $10^5$ | | RGE | |
|---|---|---|---|---|
| Supplement | − rice[1] | + rice[2] | − rice | + rice |
| 5% FBS | 18.8 | nd | 100 | nd |
| YE, 50 mg/L | 14.3 | 13.5 | 76 | 72 |
| YE, 100 mg/L | 16.1 | 13.3 | 86 | 71 |
| YE, 200 mg/L | 14.7 | 12.2 | 78 | 65 |
| YEU, 50 mg/L | 13.9 | 16.8 | 74 | 89 |
| YEU, 100 mg/L | 15.7 | 16.5 | 84 | 88 |
| YEU, 200 mg/L | 13.2 | 15.9 | 70 | 85 |

[1]"− rice" indicates medium not supplemented with 100 mg/L rice hydrolysate.
[2]"+ rice" indicates medium supplemented with 100 mg/L rice hydrolysate.

The results of these studies indicate that YEU used as a supplement promotes growth of animal cells at all concentrations tested in the present media and significantly outperforms YE, suggesting that ultrafiltration of YE to yield YEU provides a more optimal supplement for the support of animal cell cultivation. Furthermore, these results demonstrate that the combination of YEU and rice hydrolysate as supplements in the present media is preferable over the use of YEU alone, since VERO cell growth was higher in the YEU/rice combination media for all concentrations of YEU tested. Finally, since the 50 mg/liter concentration of YEU performed approximately as well as higher concentrations in rice-supplemented media, the combination of 100 mg/liter rice hydrolysate and 50 mg/liter YEU appear to be particularly favorable for economic reasons in the formulation of animal protein-free cell culture media for the cultivation of animal cells.

Example 6

Titration of rEGF

To examine the effect of growth factor concentration on the performance of the culture media, recombinant human EGF was added to the basal media of Example 1 at various concentrations. These media were then used to examine VERO cell growth as described above. Cell counts were compared to those obtained in basal medium that was unsupplemented (negative control) or to EMEM supplemented with 5% FBS (positive control). Results shown in Table 6 demonstrate mean cell count and relative growth efficiency (RGE) for each of the EGF concentrations; RGE was calculated as described in Example 2.

TABLE 6

Titration of EGF

| Supplement | Mean Cell Count, × $10^5$ | RGE |
|---|---|---|
| None | 9.9 | 42 |
| 5% FBS | 23.5 | 100 |
| EGF, 10 mg/L | 22.6 | 96 |
| EGF, 5 mg/L | 11.9 | 51 |
| EGF, 1 mg/L | 11.4 | 49 |
| EGF, 0.5 mg/L | 8.0 | 34 |

These initial results, with a wide range of EGF concentrations, suggested that a concentration of 10 mg/liter of EGF in the present media is optimal for supporting the growth of animal cells. To more closely examine this effect, these experiments were repeated with a more narrow range of EGF concentrations. The results of these studies are shown in Table 7.

TABLE 7

Titration of EGF

| Supplement | Mean Cell Count, × $10^5$ | RGE |
|---|---|---|
| 5% FBS | 26.6 | 100 |
| EGF, 10 mg/L | 19.5 | 73 |
| EGF, 9 mg/L | 20.7 | 78 |
| EGF, 8 mg/L | 21.0 | 79 |
| EGF, 7 mg/L | 19.6 | 74 |
| EGF, 6 mg/L | 19.3 | 73 |
| EGF, 5 mg/L | 20.2 | 76 |

The discrepancy between Tables 6 and 7 at the 5 mg/L concentration of EGF prompted another titration. The results in this table represent the mean cells per 25 cm² flask in duplicate over 4 subcultures.

TABLE 8

Titration of EGF

| EGF (mg/L) | Mean Cell Count, × $10^5$ | RGE* |
|---|---|---|
| 0 | 5.1 | 100 |
| 5 | 7.0 | 137 |
| 6 | 6.0 | 118 |
| 7 | 7.1 | 139 |
| 8 | 7.3 | 143 |
| 9 | 7.4 | 145 |
| 10 | 6.8 | 133 |

*as % of 0 mg/L control.

For economic reasons 5 mg/L EGF was chosen for this embodiment.

These results indicate that EGF at concentrations as low as 5 mg/L in the present culture media will support the growth of VERO cells. Concentrations lower than 5 mg/L, however, may be insufficient in the present formulations.

Taken in combination, the results shown in Examples 1–6 indicate that an optimal culture medium formulation for supporting the cultivation of animal cells is the basal medium formulation shown in Table 1, supplemented with EGF at 5–10 mg/liter, yeast extract (preferably yeast extract ultrafiltrate) at 50–100 mg/liter, and at least one plant peptide (preferably rice peptides or hydrolysate) at 100–200 mg/liter.

Table 9 shows the use of the medium to grow BHK-21 cells in suspension on a shaker platform. In this experiment, 0.2% PLURONIC F68 was added to both the test medium and the EMEM FBS 5% control to reduce shear damage. Counts were made at 72, 96 and 120 hours. As can be seen in Table 9 the test medium performed as well as or better than the control. By 120 hrs the viability began dropping much more rapidly in the control serum-supplemented medium as compared to this preferred embodiment of the present invention.

TABLE 9

Growth of BHK-21 Cells in Suspension in Shaker Flasks

| Time (hrs) | Viable cells/ml × $10^5$ EMEM 5% FBS control | Preferred Embodiment of Present Invention |
|---|---|---|
| 0 | 3.2 | 3.2 |
| 72 | 7.1 | 7.8 |
| 96 | 9.0 | 10.4 |
| 120 | 3.7 | 8.0 |

Example 7

Supplementation of Media with Plant Lipids and Fatty Acids

To determnine whether the performance of the present culture media could be further enhanced using additional plant-derived nutrients, culture media made as described in Example 1, further containing rice peptides as described in Example 3 and one or more plant-derived lipid or fatty acid formulations, were used to culture VERO cells. Cells were plated in T-25 flasks into culture media that were not supplemented with plant-derived lipids or fatty acids (control) or that were supplemented with 5 μg/ml, 0.5 μg/ml or 0.05 μg/ml of one of the following plant lipid or fatty acid mixes obtained from Matreya, Inc. (Pleasant Gap, Pa.), having constituents present in the indicated percentages:

RM-1: palmitate (6.0%), stearate (3.0%), oleate (35.0%), linoleate (50.0%), linolenate (3.0%), arachidate (3.0%)

RM-2: palmitate (7.0%), stearate (5.0%), oleate (18.0%), linoleate (36.0%), linolenate (34.0%)

RM-3: myristate (11.0%), palmitate (4.0%), stearate (3.0%), oleate (45.0%), linoleate (15.0%), linolenate (3.0%), arachidate (3.0%), behenate (3.0%), erucate (20.0%), lignocerate (3.0%)

RM-5: caprylate (7.0%), caprate (5.0%), laurate (48.0%), myristate (15.0%), palmitate (7.0%), stearate (3.0%), oleate (12.0%), linoleate (3.0%)

RM-6: myristate (2.0%), palmitate (30.0%), palmitoleate (3.0%), stearate (14.0%), oleate (41.0%), linoleate (7.0%), linolenate (3.0%)

Duplicate experiments were performed, and viable cell counts per flask were determined in cultures at passages 1, 2 and 3 and expressed as a percentage of cell counts in control media not supplemented with plant lipids. Results are shown in Table 10.

TABLE 10

Effects of Plant-Derived Lipids on Cell Growth.

| | | Average Cell Count Per Flask, × $10^5$ (% of Control) | | | | | |
|---|---|---|---|---|---|---|---|
| | | Passage 1 | | Passage 2 | | Passage 3 | |
| Supplement | Concentration | Expt 1 | Expt 2 | Expt. 1 | Expt. 2 | Expt. 1 | Expt. 2 |
| RM-1 | 5 μg/ml | 37.2 (66) | 16.8 (140) | 21.8 (111) | 15.7 (122) | ND (not done) | 22.4 (117) |
| | 0.5 μg/ml | 52.5 (94) | 15.8 (133) | 25.0 (127) | 8.8 (293) | ND | 18.2 (131) |
| | 0.05 μg/ml | 28.1 (146) | ND | 8.6 (116) | ND | 11.9 (134) | ND |
| RM-2 | 5 μg/ml | 21.3 (38) | 16.2 (135) | 30.3 (154) | 15.3 (119) | ND | 24.1 (126) |
| | 0.5 μg/ml | 58.0 (104) | 15.0 (126) | 16.4 (83) | 6.5 (217) | ND | 17.2 (124) |
| | 0.05 μg/ml | 28.1 (146) | ND | 8.8 (119) | ND | 7.6 (85) | ND |
| RM-3 | 5 μg/ml | 42.2 (75) | 16.2 (135) | 20.2 (102) | 14.4 (112) | ND | 20.9 (109) |
| | 0.5 μg/ml | 28.2 (50) | 10.9 (92) | 17.9 (91) | 2.6 (87) | ND | 7.9 (57) |
| | 0.05 μg/ml | 27.7 (144) | ND | 9.2 (124) | ND | 6.7 (75) | ND |
| RM-5 | 5 μg/ml | 31.3 (56) | 12.0 (100) | 20.1 (102) | 17.6 (136) | ND | 23.2 (121) |
| | 0.5 μg/ml | 55.0 (98) | 7.8 (66) | 21.0 (106) | 3.5 (117) | ND | 17.7 (127) |
| | 0.05 μg/ml | 24.0 (124) | ND | 7.1 (96) | ND | 9.2 (103) | ND |
| RM-6 | 5 μg/ml | 32.8 (58) | 12.0 (100) | 18.5 (94) | 12.9 (100) | ND | 19.2 (100) |
| | 0.5 μg/ml | 54.0 (96) | 8.1 (68) | 21.2 (108) | 5.4 (180) | ND | 14.5 (104) |
| | 0.05 μg/ml | 23.7 (123) | ND | 10.4 (140) | ND | 8.4 (94) | ND |
| Control | 5 μg/ml | 56.0 (100) | 12.0 (100) | 19.7 (100) | 12.9 (100) | ND | 19.2 (100) |
| | 0.5 μg/ml | 56.0 (100) | 11.9 (100) | 19.7 (100) | 3.0 (100) | ND | 13.9 (100) |
| | 0.05 μg/ml | 19.3 (100) | ND | 7.4 (100) | ND | 8.9 (100) | ND |

These results indicate that supplementation of culture media with plant-derived lipid/fatty acid mixtures enhances the growth of VERO cells when compared to control media not containing these lipid/fatty acid mixes. Use of most of the plant lipid/fatty acid mixtures at concentrations of 0.05 to 5 µg/ml in the culture media induced a substantial increase in VERO cell growth over three passages, with the RM-1 mixture apparently providing the most significant increases at each passage. Together with those from the foregoing Examples, these results indicate that cell culture media comprising a combination of plant-derived nutrients, such as plant peptides and plant lipids or fatty acids, are useful in supporting cultivation and growth of mammalian cells.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An animal cell culture medium comprising at least one peptide derived from rice, wherein said animal cell culture medium is completely devoid of animal-derived proteins, and wherein said medium is capable of supporting the cultivation of an animal cell in vitro.

2. The animal cell culture medium of claim 1, said medium further comprising an enzymatic digest or extract of yeast cells.

3. The animal cell culture medium of claim 1 or claim 2, wherein said medium further comprises at least one plant-derived lipid or at least one plant-derived fatty acid.

4. The animal cell culture medium of claim 1 or claim 2, wherein said medium is a 1× medium formulation.

5. The animal cell culture medium of claim 1 or claim 2, wherein said medium is a 10×–100× medium formulation.

6. The animal cell culture medium of claim 1 or claim 2, said medium further comprising at least one ingredient selected from the group of ingredients consisting of at least one amino acid, at least one vitamin, at least one inorganic salt, at least one trace element, at least one plant lipid or fatty acid, adenine sulfate ATP, deoxyribose, ethanolamine, D-glucose, glutathione, N-(2-hydroxyethyl)piperazine-N'-(2-ethanesulfonic acid) (HEPES), hypoxanthine, linoleic acid, lipoic acid, phenol red, phosphoethanolamine, putrescine, sodium pyruvate, thymidine, uracil and xanthine.

7. The animal cell culture medium of claim 6, wherein said amino acid ingredient comprises one or more amino acids selected from the group consisting of L-alanine, L-arginine, L-asparagine, L-aspartic acid, L-cystine, L-cysteine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine.

8. The animal cell culture medium of claim 6, wherein said vitamin ingredient comprises one or more vitamins selected from the group consisting of ascorbic acid magnesium salt, biotin, choline chloride, D-Ca$^{++}$-pantothenate, folic acid, i-inositol, menadione, niacinamide, nicotinic acid, paraaminobenzoic acid (PABA), pyridoxal, pyridoxine, riboflavin, thiamine, vitamin A acetate, vitamin B$_{12}$ and vitamin D$_2$.

9. The animal cell culture medium of claim 6, wherein said inorganic salt ingredient comprises one or more inorganic salts selected from the group consisting of CaCl$_2$, KCl, MgCl$_2$, MgSO$_4$, NaCl, NaHCO$_3$, Na$_2$HPO$_4$, NaH$_2$PO$_4$ and ferric citrate chelate.

10. The animal cell culture medium of claim 6, wherein said trace element ingredient comprises an ion of one or more trace elements selected from the group consisting of barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc and aluminum.

11. An animal cell culture medium obtained by combining at least one peptide derived from rice together with an animal cell culture medium, wherein said animal cell culture medium is completely devoid of animal-derived proteins, and wherein said medium is capable of supporting the cultivation of an animal cell in vitro.

12. The animal cell culture medium obtained according to claim 11, wherein said medium is obtained by further combining said animal cell culture medium with an enzymatic digest or extract of yeast cells.

13. The animal cell culture medium obtained according to claim 11 or claim 12, wherein said medium is obtained by further combining said animal cell culture medium with a at least one plant-derived lipid or at least one plant-derived fatty acid.

14. The animal cell culture medium obtained according to claim 11, wherein said medium is obtained by combining one or more additional ingredients selected from the group consisting of adenine sulfate, ATP, deoxyribose, ethanolamine•HCl, D-glucose, glutathione, N-(2-hydroxyethyl)piperazine-N'-(2-ethanesulfonic acid) (HEPES), hypoxanthine, linoleic acid, lipoic acid, phenol red, phosphocthanolamine, putrescine, sodium pyruvate, thymidine, uracil, xanthine, L-alanine, L-arginine, L-asparagine, L-aspartic acid, L-cystine, L-cysteine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, ascorbic acid magnesium salt, biotin, choline chloride, D-Ca$^{++}$-pantothenate, folic acid, i-inositol, menadione, niacinamide, nicotinic acid, paraaminobenzoic acid (PABA), pyridoxal, pyridoxine, riboflavin, thiamine, vitamin A acetate, vitamin B$_{12}$, vitamin D$_2$, CaCl$_2$, KCl, MgCl$_2$, MgSO$_4$, NaCl, NaHCO$_3$, Na$_2$HPO$_4$, NaH$_2$PO$_4$, Ba(C$_2$H$_3$O$_2$)$_2$, KBr, CoCl$_2$, KI, MnCl$_2$, Cr(SO$_4$)$_3$, CuSO$_4$, NiSO$_4$, H$_2$SeO$_3$, NaVO$_3$, TiCl$_4$, GeO$_2$, (NH$_4$)$_6$Mo$_7$O$_{24}$, Na$_2$SiO$_3$, FeSO$_4$, NaF, AgNO$_3$, RbCl, SnCl$_2$, ZrOCl$_2$, CdSO$_4$, ZnSO$_4$, Fe(NO$_3$)$_3$, AlCl$_3$ and ferric citrate chelate, wherein each ingredient is present in an amount which supports the cultivation of an animal cell in vitro.

15. The animal cell culture medium of claim 3, wherein said plant-derived lipid or fatty acid is selected from the group consisting of palmitate, stearate, oleate, linoleate, linolenate, arachidate, myristate, behenate, erucate, lignocerate, caprylate, caprate, laurate and palmitoleate, and combinations thereof.

16. The animal cell culture medium of claim 13, wherein said plant-derived lipid or fatty acid is selected from the group consisting of palmitate, stearate, oleate, linoleate, linolenate, arachidate, myristate, behenate, erucate, lignocerate, caprylate, caprate, laurate and palmitoleate, and combinations thereof.

17. The animal cell culture medium of any one of claims 1 or 11, wherein said animal cell is selected from the group of animal cells consisting of an insect cell, an avian cell, a mammalian cell and a fish cell.

18. The animal cell culture medium of claim 12, wherein said insect cell is derived from Spodoptera spp. or Trichoplusa spp.

19. The animal cell culture medium of claim 12, wherein said mammalian cell is a human cell, a hybridoma cell, a CHO cell, a BHK cell, a COS cell, a VERO cell, a HeLa cell, a 293 cell, a PER-C6 cell, a K562 cell, a MOLT-4 cell, an M1 cell, an NS-1 cell, a COS-7 cell, an MDBK cell, an MDCK cell, an MRC-5 cell, a WI-38 cell, a WEHI cell, an SP2/0 cell, or a derivative thereof.

20. A method of cultivating an animal cell comprising the steps of
(a) contacting said animal cell with the animal cell culture medium of any one of claims 1, 2, 11 and 12; and
(b) cultivating said animal cell under conditions suitable to support cultivation of said animal cell.

21. The method of claim 20, wherein said animal cell is selected from the group of animal cells consisting of an insect cell, an avian cell, a mammalian cell and a fish cell.

22. A composition comprising the animal cell culture medium of any one of claims 1 or 11, and an animal cell.

23. The composition of claim 22, wherein said animal cell is selected from the group of animal cells consisting of an insect cell, an avian cell, a mammalian cell and a fish cell.

24. The composition of claim 22, wherein said mammalian cell is a human cell, a hybridoma cell, a CHO cell, a BHK cell, a COS cell, a VERO cell, a HeLa cell, a 293 cell, a PER-C6 cell, a K562 cell, a MOLT-4 cell, an M1 cell, an NS-1 cell, a COS-7 cell, an MDBK cell, an MDCK cell, an MRC-5 cell, a WI-38 cell, a WEHI cell, an SP2/0 cell, or a derivative thereof.

25. The animal cell culture medium of claim 1 or claim 11, wherein said at least one peptide derived from rice is present at a concentration of about 10 mg/liter to about 1000 mg/liter.

26. The animal cell culture medium of claim 1 or claim 11, wherein said at least one peptide derived from rice is present at a concentration of about 100 mg/liter to about 200 mg/liter.

* * * * *